United States Patent [19]

Stetter et al.

[11] Patent Number: 4,772,310
[45] Date of Patent: Sep. 20, 1988

[54] 5-ACYLAMINO-PYRAZOLE DERIVATIVES, COMPOSITION CONTAINING THEM, AND THEIR USE AS HERBICIDES AND PLANT GROWTH

[75] Inventors: Jörg Stetter, Wuppertal; Otto Schallner, Monheim; Reinhold Gehring, Wuppertal; Hans-Joachim Santel, Leverkusen; Robert R. Schmidt, Bergisch Gladbach; Klaus Lürssen, Bergisch Gladbach, all of Fed. Rep. of Germany

[73] Assignee: Bayer Aktiengesellschaft, Leverkusen, Fed. Rep. of Germany

[21] Appl. No.: 52,671

[22] Filed: May 19, 1987

[30] Foreign Application Priority Data

Jun. 4, 1986 [DE] Fed. Rep. of Germany ....... 3618717

[51] Int. Cl.4 ................. A01N 43/56; C07D 231/40; C07D 401/04
[52] U.S. Cl. ............................. 71/92; 546/279; 548/362; 548/375; 548/376
[58] Field of Search .............. 548/376, 375, 362; 71/92; 546/279

[56] References Cited

U.S. PATENT DOCUMENTS 4,545,809 10/1985 Seki et al. .................. 548/375
4,711,658 12/1987 Gehring et al. ............. 548/376

Primary Examiner—Mary C. Lee
Assistant Examiner—Kurt G. Briscoe
Attorney, Agent, or Firm—Sprung Horn Kramer & Woods

[57] ABSTRACT

Herbicidal and plant growth-regulating novel 5-acylamino-pyrazoles of the formula

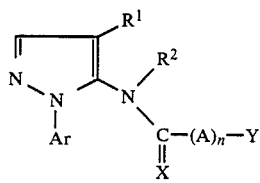

in which
$R^1$ represents hydrogen, halogen or nitro,
$R^2$ represents hydrogen, alkyl, alkenyl, alkinyl or optionally substituted cycloalkyl,
Ar represents in each case optionally substituted phenyl or pyridyl,
X represents oxygen or sulphur,
A represents a straight-chain or branched optionally substituted alkylene bridge,
n represents the numbers 0 or 1 and
Y represents cyano or the grouping

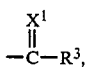

wherein
$X^1$ represents oxygen or sulphur and
$R^3$ represents hydroxyl, alkoxy, alkenyloxy, alkynyloxy, alkylthio, amino, alkylamino, dialkylamino, alkenylamino, dialkenylamino, alkylalkenylamino or a —OM radical,
wherein M represents one equivalent of the cation of an inorganic or organic base.

Intermediates therefor of the formula

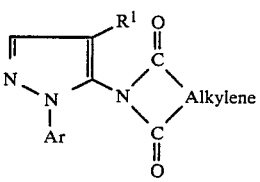

are also new.

13 Claims, No Drawings

5-ACYLAMINO-PYRAZOLE DERIVATIVES, COMPOSITION CONTAINING THEM, AND THEIR USE AS HERBICIDES AND PLANT GROWTH

The invention relates to new 5-acylamino-pyrazole derivatives, several processes for their preparation and their use as herbicides and growth regulators.

It is already known that certain 5-acylamido-1-aryl-pyrazoles, such as, for example, 4-cyano-5-propionamido-1-(2,4,6-trichlorophenyl)-pyrazole, have herbicidal properties (compare, for example, DE-OS (German Published Specification) No. 3,226,513).

However, the herbicidal activity of these already known compounds against weeds, like their tolerance towards important crop plants, is not always completely satisfactory in all fields of use.

New 5-acylamino-pyrazole derivatives of the general formula (I)

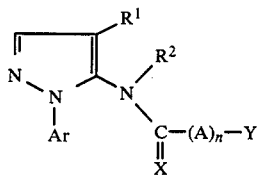

in which
$R^1$ represents hydrogen, halogen or nitro,
$R^2$ represents hydrogen, alkyl, alkenyl, alkinyl or optionally substituted cycloalkyl,
Ar represents in each case optionally substituted phenyl or pyridyl,
X represents oxygen or sulphur,
A represents a straight-chain or branched optionally substituted alkylene bridge,
n represents the numbers 0 or 1 and
Y represents cyano or the grouping

wherein
$X^1$ represents oxygen or sulphur and
$R^3$ represents hydroxyl, alkoxy, alkenyloxy, alkinyloxy, alkylthio, amino, alkylamino, dialkylamino, alkenylamino, dialkenylamino, alkylalkenylamino or a —OM radical,
wherein M represents one equivalent of the cation of an inorganic or organic base,
have been found.

It has furthermore been found that the new 5-acylamino-pyrazole derivatives of the formula (I)

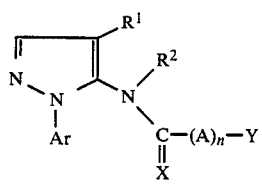

in which
$R^1$ represents hydrogen, halogen or nitro,
$R^2$ represents hydrogen, alkyl, alkenyl, alkinyl or optionally substituted cycloalkyl,
Ar represents in each case optionally substituted phenyl or pyridyl,
X represents oxygen or sulphur,
A represents a straight-chain or branched optionally substituted alkylene bridge,
n represents the numbers 0 or 1 and
Y represents cyano or the grouping

wherein
$X^1$ represents oxygen or sulphur and
$R^3$ represents hydroxyl, alkoxy, alkenyloxy, alkinyloxy, alkylthio, amino, alkylamino, dialkylamino, alkenylamino, dialkenylamino, alkylalkenylamino or an OM radical,
wherein M represents one equivalent of the cation of an inorganic or organic base,
are obtained with the aid of the processes described below:

(a) 5-acylamino-pyrazole derivatives of the formula (Ia)

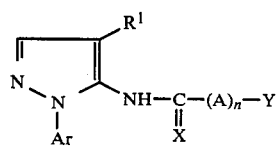

in which $R^1$, X, Y, A, Ar and the index n have the abovementioned meaning, are obtained by a process in which 5-amino-1-aryl-pyrazoles of the formula (II)

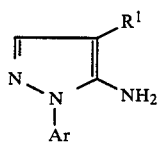

in which $R^1$ and Ar have the abovementioned meaning, are reacted with acylating agents of the formula (III)

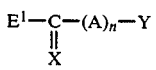

in which
X, Y, A and the index n have the abovementioned meaning and
$E^1$ represents an electron-withdrawing leaving group,
if appropriate in the presence of a diluent, if appropriate in the presence of an acid-binding agent and if appropriate in the presence of a catalyst;

(b) 5-acylamino-pyrazole derivatives of the formula (Ib)

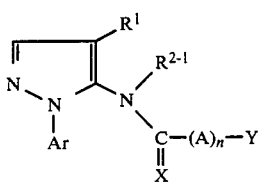

in which
R¹, X, Y, A, the index n and Ar have the abovementioned meaning and
R²⁻¹ represents alkyl, alkenyl, alkinyl or optionally substituted cycloalkyl, are obtained by a process in which the 5-acylamino-pyrazole derivatives obtainable by process (a), of the formula (Ia)

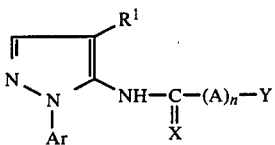

in which R¹, X, Y, A, Ar and the index n have the abovementioned meaning, are reacted with alkylating agents of the formula (IV)

$$E^2—R^{2-1} \quad (IV)$$

in which
R²⁻¹ has the abovementioned meaning and
E² represents halogen, or represents optionally substituted alkoxysulphonyloxy, or represents optionally substituted arylsulphonyloxy, if appropriate in the presence of a diluent and if appropriate in the presence of an acid-binding agent, and if appropriate in the presence of a catalyst;

(c) 5-acylamino-pyrazole derivatives of the formula (Ic)

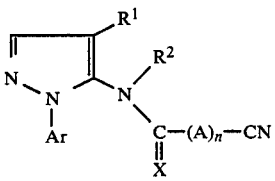

in which R¹, R², Ar, X, A and the index n have the above-mentioned meaning, are obtained by a process in which 5-acylamido-1-arylpyrazoles of the formula (V)

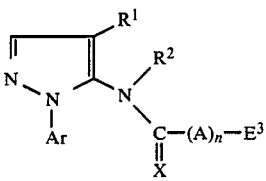

in which
R¹, R², Ar, X, A and the index n have the above-mentioned meaning and
E³ represents halogen, are reacted with cyano derivatives of the formula (VI)

$$W—CN \quad (VI)$$

in which W represents hydrogen or one equivalent of an alkaline earth metal cation or alkali metal cation, or represents one equivalent of the cation of an organic base, if appropriate in the presence of a diluent and if appropriate in the presence of an acid-binding agent, and if appropriate in the presence of a catalyst;

(d) 5-acylamino-pyrazole derivatives of the formula (Id)

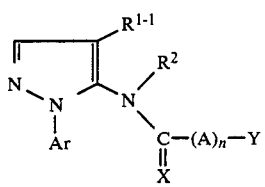

in which
R², X, A, Y, Ar and the index n have the above-mentioned meaning and
R¹⁻¹ represents halogen or nitro, are obtained by a process in which the 5-acylamino-pyrazole derivatives obtainable with the aid of processes (a), (b), (c), (e) or (f), of the formula (Ie)

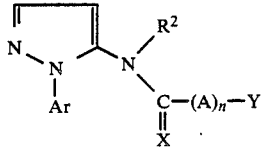

in which R², X, Y, A, Ar and the index n have the abovementioned meaning, are reacted with halogenating or nitrating agents of the formula (VII)

$$R^{1-1}—E^4 \quad (VII)$$

in which
R¹⁻¹ has the abovementioned meaning and
E⁴ represents an electron-withdrawing leaving group, if appropriate in the presence of a diluent and if appropriate in the presence of a catalyst or reaction auxiliary;

(e) 5-acylamino-pyrazole derivatives of the formula (If)

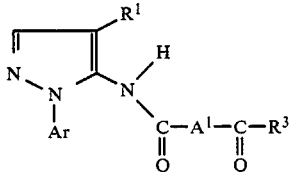

in which
r¹, R³ and Ar have the abovementioned meaning and
A¹ represents straight-chain or branched alkylene with 1 to 6 carbon atoms, are obtained by a process in which 5-imido-pyrazoles of the formula (VIII)

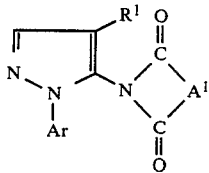 (VIII)

in which $R^1$, Ar, and $A^1$ have the abovementioned meaning, are reacted with nucleophilic compounds of the formula (IX)

 (IX)

in which $R^3$ has the abovementioned meaning, if appropriate in the presence of a diluent and if appropriate in the presence of a reaction auxiliary;

(f) 5-acylamino-pyrazole derivatives of the formula (Ig)

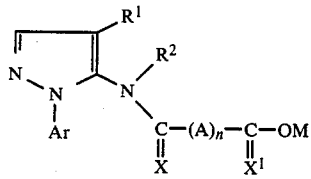 (Ig)

in which $R^1$, $R^2$, Ar, A, X, $X^1$, M and the index n have the abovementioned meaning, are obtained by a process in which the 5-acylamino-pyrazole derivatives obtainable by processes (a), (b), (d) or (e), of the formula (Ih)

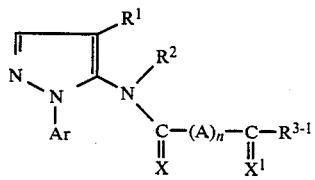 (Ih)

in which
$R^1$, $R^2$, Ar, X, $X^1$, A and the index n have the abovementioned meaning and
$R^{3-1}$ represents hydroxyl or alkoxy, are neutralized or hydrolyzed with the hydroxides or carbonates of alkali metals or alkaline earth metals or neutralized with organic bases.

Finally, it has been found that the new 5-acylamino-pyrazole derivatives of the general formula (I) have herbicidal properties, and in particular also selectively herbicidal and growth-regulating properties. Surprisingly, the 5-acylamino-pyrazole derivatives of the general formula (I) according to the invention exhibit a considerably better general herbicidal activity against problem weeds which are difficult to combat and at the same time a clearly improved tolerance towards important crop plants in comparison with the 5-acylamido-1-aryl-pyrazoles known from the prior art, such as, for example, 4-cyano-5-propionamido-1-(2,4,6-trichlorophenyl)-pyrazole, which are closely related compounds chemically and from the point of view of their action.

Formula (I) provides a general definition of the 5-acylamino-pyrazole derivatives according to the invention. Preferred compounds of the formula (I) are those in which $R^1$ represents hydrogen, nitro, fluorine, chlorine, bromine or iodine;

$R^2$ represents hydrogen, or represents straight-chain or branched alkyl with 1 to 12 carbon atoms, or represents in each case straight-chain or branched alkenyl or alkinyl with in each case 3 to 8 carbon atoms, or represents cycloalkyl which has 3 to 8 carbon atoms and is optionally substituted by alkyl with 1 to 4 carbon atoms;

Ar represents phenyl, 2-pyridyl, 3-pyridyl or 4-pyridyl, in each case optionally monosubstituted or polysubstituted by identical or different substituents, possible substituents in each case being: halogen, cyano, nitro, in each case straight-chain or branched alkyl, alkoxy and alkoxycarbonyl with in each case 1 to 4 carbon atoms in the alkyl parts, in each case straight-chain or branched halogenoalkyl and halogenoalkoxy with in each case 1 to 4 carbon atoms and 1 to 9 identical or different halogen atoms and an $-S(O)_m-R^4$ radical,
wherein $R^4$ represents amino, or represents in each case straight-chain or branched alkyl, alkylamino, dialkylamino or halogenoalkyl with in each case 1 to 4 carbon atoms in the individual alkyl parts and in the case of the halogenoalkyl with 1 to 9 identical or different halogen atoms and m represents the number 0, 1 or 2; and X represents oxygen or sulphur;

A represents a straight-chain or branched alkylene bridge which has 1 to 6 carbon atoms and is optionally monosubstituted or polysubstituted by identical or different substituents from the group comprising halogen and phenyl, which is optionally substituted by halogen or alkyl with 1 to 4 carbon atoms;

n represents the number 0 or 1 and

Y represents cyano or the grouping

wherein $X^1$ represents oxygen or sulphur and $R^3$ represents hydroxyl, in each case straight-chain or branched alkoxy or alkylthio with in each case 1 to 6 carbon atoms, in each case straight-chain or branched alkenyloxy or alkinyloxy with in each case 3 to 8 carbon atoms, amino, in each case straight-chain or branched alkylamino or dialkylamino with in each case 1 to 6 carbon atoms in the alkyl parts, in each case straight-chain or branched alkenylamino or dialkenylamino with in each case 3 to 8 carbon atoms in the alkenyl parts or straight-chain or branched alkyl-alkenylamino with 1 to 6 carbon atoms in the alkyl part and 3 to 8 carbon atoms in the alkenyl part, or represents an —OM radical,
wherein M represents one equivalent of an alkaline earth metal cation or alkali metal cation, or represents ammonium which is optionally mono-, di-, tri- or tetrasubstituted by identical or different substituents from the group comprising straight-chain or branched alkyl with 1 to 12 carbon atoms and benzyl.

Particularly preferred 5-acylamino-pyrazole derivatives of the formula (I) are those in which $R^1$ represents hydrogen, nitro, chlorine or bromine, $R^2$ represents hydrogen, or represents straight-chain or branched alkyl with 1 to 8 carbon atoms, or represents in each case straight-chain or branched alkenyl or alkinyl with in each case 3 to 6 carbon atoms, or represents cycloalkyl which has 3 to 6 carbon atoms and is optionally substituted by methyl, ethyl or isopropyl;

Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and an —S(O)$_m$—R$^4$ radical, wherein $R^4$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents the number 0, 1 or 2, and X represents oxygen or sulphur;

A represents a bridge member of the formula $$-CH_2-;\ -CH_2-CH_2-;\ -\underset{CH_3}{\underset{|}{CH}}-;\ -CCl_2-CH_2-;$$

$$-CHCl-CH_2-,\ -\underset{CH_3}{\underset{|}{CH}}-CH_2-;\ -CH_2-CH_2-CH_2-;$$

$$-CH_2-CH_2-CH_2-CH_2-;\ -\underset{CH_3}{\overset{CH_3}{\underset{|}{\overset{|}{C}}}}-CH_2-;\ -\underset{Br}{\underset{|}{CH}}-CH_2-;$$

$$-CBr_2-CH_2-;\ -C(CH_3)_2-;\ -\underset{CH_3}{\underset{|}{CH}}-\underset{CH_3}{\underset{|}{CH}}-;\ -\overset{H}{\underset{|}{C}}-$$

[phenyl]

$$-\overset{H}{\underset{|}{C}}-CH_2-$$

[phenyl]

n represents the number 0 or 1 and

Y represents cyano or the grouping $$-\overset{X^1}{\underset{|}{\overset{\|}{C}}}-R^3,$$

wherein $X^1$ represents oxygen and $R^3$ represents hydroxyl, alkoxy with 1 to 3 carbon atoms, alkenyloxy or alkinyloxy with in each case 3 to 6 carbon atoms, amino, alkylamino or dialkylamino with in each case 1 to 3 carbon atoms in each alkyl part, alkenylamino or dialkenylamino with in each case 3 to 6 carbon atoms in each alkenyl part or alkyl-alkenylamino with 1 to 3 carbon atoms in the alkyl part and 3 to 6 carbon atoms in the alkenyl part, or represents an —OM radical, wherein M represents one equivalent of a sodium, potassium, calcium, magnesium or barium cation, or represents an isopropylammonium dimethylbenzylammonium, triethylammonium or tributylammonium ion.

Especially preferred 5-acylamino-pyrazole derivatives of the formula (I) are those in which $R^1$ represents hydrogen or nitro;

$R^2$ represents hydrogen, methyl, ethyl, allyl, propargyl or cyclohexyl;

Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, difluorochloroethyl, chloroethyl, dichloromethyl, difluoromethyl, pentafluoroethyl, tetrafluoroethyl, trifluorochloroethyl, trifluoroethyl, difluorodichloroethyl, trifluorodichloroethyl pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R$^4$ radical, wherein $R^4$ represents amino, methylamino, ethylamino, dimethylamino, diethylamino, fluorodichloromethyl, difluoromethyl, tetrafluoroethyl, trifluorochloroethyl, trifluoromethyl, methyl or ethyl and m represents the number 0, 1 or 2, and X represents oxygen or sulphur;

A represents a bridge member of the formula

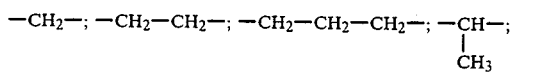
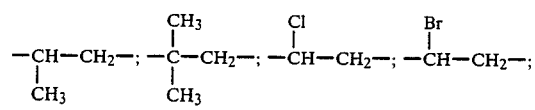
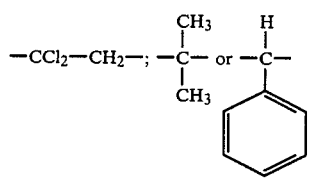

n represents the number 0 or 1 and
Y represents cyano or the grouping

$X^1$ represents oxygen and
$R^3$ represents hydroxyl, methoxy, ethoxy, n- or i-propoxy, allyloxy, propargyloxy, amino, methylamino, dimethylamino, allylamino, diallylamino, methylethylamino, methyl-allylamino or an -OM radical,
wherein
M represents one equivalent of a sodium, potassium or calcium cation, or represents an isopropylammonium ion.

The following 5-acylamino-pyrazole derivatives of the general formula (I) may be mentioned specifically, in addition to the compounds mentioned in the Preparation Examples:

TABLE 1 (I)

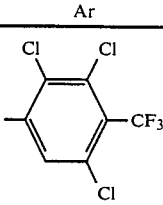

| $R^1$ | $R^2$ | X | n | A | Y | Ar |
|---|---|---|---|---|---|---|
| H | H | O | 0 | — | COOH | 2,6-Cl$_2$-4-CF$_3$-3-Cl-phenyl |
| H | H | O | 0 | — | COONa | 2,6-Cl$_2$-4-CF$_3$-3-Cl-phenyl |
| H | H | O | 0 | — | COOK | 2,6-Cl$_2$-4-CF$_3$-3-Cl-phenyl |
| H | H | O | 0 | — | COONH$_3$C$_3$H$_7$—i | 2,6-Cl$_2$-4-CF$_3$-3-Cl-phenyl |
| NO$_2$ | H | O | 0 | — | COOH | 2,6-Cl$_2$-4-CF$_3$-3-Cl-phenyl |

TABLE 1-continued
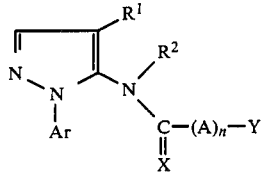
| R¹ | R² | X | n | A | Y | Ar |
|---|---|---|---|---|---|---|
| NO₂ | H | O | 0 | — | COONa | 2,3,5-Cl₃-4-CF₃-C₆H |
| NO₂ | H | O | 0 | — | COOK | 2,3,5-Cl₃-4-CF₃-C₆H |
| NO₂ | H | O | 0 | — | COONH₃C₃H₇—i | 2,3,5-Cl₃-4-CF₃-C₆H |
| NO₂ | H | O | 0 | — | COOH | 2,3,5,6-F₄-4-CF₃-C₆ |
| NO₂ | H | O | 0 | — | COOCH₃ | 2,3,5,6-F₄-4-CF₃-C₆ |
| NO₂ | H | O | 0 | — | COOC₂H₅ | 2,3,5,6-F₄-4-CF₃-C₆ |
| NO₂ | H | O | 0 | — | COOCH₃ | 2,3,5-Cl₃-4-CF₃-C₆H |
| NO₂ | H | O | 0 | — | COOC₂H₅ | 2,3,5-Cl₃-4-CF₃-C₆H |

TABLE 1-continued (I)

| R¹ | R² | X | n | A | Y | Ar |
|----|----|----|----|----|----|----|
| NO₂ | H | O | 0 | — | COOCH₃ | 3-Br, 4-(substituent), 5-Cl, with CF₃ at 4-position (Br, Cl, CF₃ substituted phenyl) |
| NO₂ | H | O | 0 | — | COOC₂H₅ | Br, Cl, CF₃ substituted phenyl |
| NO₂ | H | O | 0 | — | COOH | Br, Cl, CF₃ substituted phenyl |
| NO₂ | H | O | 0 | — | COONa | Br, Cl, CF₃ substituted phenyl |
| NO₂ | H | O | 0 | — | COOCH₃ | Br, CF₃ substituted phenyl |
| NO₂ | H | O | 0 | — | COOH | Br, CF₃ substituted phenyl |
| NO₂ | H | O | 0 | — | COOCH₃ | Cl, CF₃ substituted phenyl |
| NO₂ | H | O | 0 | — | COOC₂H₅ | Cl, CF₃ substituted phenyl |
| NO₂ | H | O | 0 | — | COOH | Cl, CF₃ substituted phenyl |

TABLE 1-continued
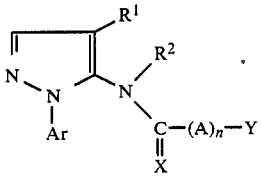
(I)
| R¹ | R² | X | n | A | Y | Ar |
|---|---|---|---|---|---|---|
| NO₂ | H | O | 0 | — | COOCH₃ | 2,5-Cl₂-3-F-4-CF₃-C₆H |
| NO₂ | H | O | 0 | — | COOC₂H₅ | 2,5-Cl₂-3-F-4-CF₃-C₆H |
| NO₂ | H | O | 0 | — | COOH | 2,5-Cl₂-3-F-4-CF₃-C₆H |
| NO₂ | H | O | 0 | — | COOCH₃ | 2,4-Cl₂-3,5-F₂-... |
| NO₂ | H | O | 0 | — | COOH | 2,4-Cl₂-3,5-F₂-... |
| NO₂ | H | O | 0 | — | COOCH₃ | 3-Cl-5-F-4-CF₃ |
| NO₂ | H | O | 0 | — | COOH | 3-Cl-5-F-4-CF₃ |
| NO₂ | H | O | 1 | CH₂ | CN | 2,3,5-Cl₃-4-CF₃ |

TABLE 1-continued
(I)
| R¹ | R² | X | n | A | Y | Ar |
|---|---|---|---|---|---|---|
| $NO_2$ | H | O | 1 | —CH(CH₃)— | CN | 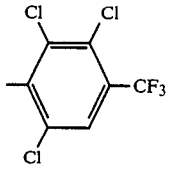 2,6-dichloro-4-CF₃-phenyl |
| $NO_2$ | H | O | 1 | —CH₂— | CN |  2,6-dichloro-3-fluoro-4-CF₃-phenyl |
| $NO_2$ | H | O | 1 | —CH(CH₃)— | CN | 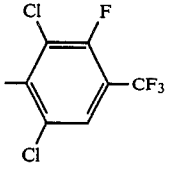 2,6-dichloro-3-fluoro-4-CF₃-phenyl |
| $NO_2$ | H | O | 1 | —CH₂— | CN |  pentafluoro-4-CF₃-phenyl |
| $NO_2$ | H | O | 1 | —CH(CH₃)— | CN | 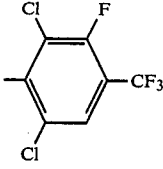 pentafluoro-4-CF₃-phenyl |
| $NO_2$ | H | O | 1 | —CH₂— | CN |  2,6-dichloro-4-SCF₃-phenyl |
| $NO_2$ | H | O | 1 | —CH₂— | CN | 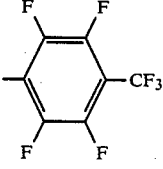 2,6-dichloro-4-SO₂CF₃-phenyl |
| $NO_2$ | H | O | 1 | —CH₂— | CN |  2-chloro-4-OCF₃-phenyl |

TABLE 1-continued (I)
structure with R¹, R², Ar, N-N, C=X, (A)n-Y

| R¹ | R² | X | n | A | Y | Ar |
|---|---|---|---|---|---|---|
| NO₂ | H | O | 1 | —CH₂— | CN | 2,6-dichloro-3,5-difluoro-4-CF₃-phenyl |
| NO₂ | H | O | 1 | —CH₂— | CO₂CH₃ | 2,3,6-trichloro-4-CF₃-phenyl |
| NO₂ | H | O | 1 | —CH(CH₃)— | —CO₂CH₃ | 2,3,6-trichloro-4-CF₃-phenyl |
| NO₂ | H | O | 1 | —C(CH₃)₂— | CO₂CH₃ | 2,3,6-trichloro-4-CF₃-phenyl |
| NO₂ | H | O | 1 | —CH₂— | COOH | 2,3,6-trichloro-4-CF₃-phenyl |
| NO₂ | H | O | 1 | —CH(CH₃)— | COOH | 2,3,6-trichloro-4-CF₃-phenyl |
| NO₂ | H | O | 1 | —CH₂— | CO₂CH₃ | 2,3,5,6-tetrafluoro-4-CF₃-phenyl |
| NO₂ | H | O | 1 | —CH₂— | CO₂C₂H₅ | 2,3,5,6-tetrafluoro-4-CF₃-phenyl |

TABLE 1-continued (I)

$$\text{structure with pyrazole ring: N-N(Ar), C-R}^1\text{, C-N(R}^2\text{)C(=X)-(A)}_n\text{-Y}$$

| R¹ | R² | X | n | A | Y | Ar |
|---|---|---|---|---|---|---|
| NO₂ | H | O | 1 | —CH₂— | COOH | 2,3,5,6-tetrafluoro-4-CF₃-phenyl |
| NO₂ | H | O | 1 | —CH(CH₃)— | CO₂C₂H₅ | 2,3,5,6-tetrafluoro-4-CF₃-phenyl |
| NO₂ | H | O | 1 | —CH₂— | CO₂C₂H₅ | 2,5-dichloro-3-fluoro-4-CF₃-phenyl |
| NO₂ | H | O | 1 | —CH(CH₃)— | CO₂C₂H₅ | 2,5-dichloro-3-fluoro-4-CF₃-phenyl |
| NO₂ | H | O | 1 | —CH₂CH₂— | CN | 2,6-dichloro-4-CF₃-phenyl |
| NO₂ | H | O | 1 | —CH₂CH₂— | CO₂CH₃ | 2,6-dichloro-4-CF₃-phenyl |
| NO₂ | H | O | 1 | —CH(CH₃)CH(CH₃)— | CO₂CH₃ | 2,6-dichloro-4-CF₃-phenyl |
| NO₂ | H | O | 1 | —CH(CH₃)CH(CH₃)— | COOH | 2,6-dichloro-4-CF₃-phenyl |

TABLE 1-continued

Structure (I):
Pyrazole with R¹ at 4-position, N-R² and N-Ar substituents, and C(=X)-(A)$_n$-Y group on the nitrogen bearing R².

| R¹ | R² | X | n | A | Y | Ar |
|---|---|---|---|---|---|---|
| NO$_2$ | H | O | 1 | -CH(CH$_3$)-CH(CH$_3$)- | COOC$_2$H$_5$ | 2,5-dichloro-4-(trifluoromethyl)phenyl |
| NO$_2$ | H | O | 1 | CH$_2$CH$_2$ | CN | 2,3,5,6-tetrachloro-4-(trifluoromethyl)phenyl |
| NO$_2$ | H | O | 1 | CH$_2$CH$_2$ | COCH$_3$ | 2,3,5,6-tetrachloro-4-(trifluoromethyl)phenyl |
| NO$_2$ | H | O | 1 | -CH$_2$CH$_2$- | COOC$_2$H$_5$ | 2,3,5,6-tetrachloro-4-(trifluoromethyl)phenyl |
| NO$_2$ | H | O | 1 | CH$_2$CH$_2$ | COOH | 2,3,5,6-tetrachloro-4-(trifluoromethyl)phenyl |
| NO$_2$ | H | O | 1 | -CH$_2$- | CN | 2,3,5,6-tetrafluoro-4-(trifluoromethyl)phenyl |
| NO$_2$ | H | O | 1 | -CH$_2$- | COOCH$_3$ | 2,3,5,6-tetrafluoro-4-(trifluoromethyl)phenyl |
| NO$_2$ | H | O | 1 | -CH$_2$- | COOC$_2$H$_5$ | 2,3,5,6-tetrafluoro-4-(trifluoromethyl)phenyl |

TABLE 1-continued $$\text{(I)}$$

Structure: pyrazole with N-N-Ar, R¹ at 4-position, NR² at 5-position bearing C(=X)-(A)ₙ-Y

| R¹ | R² | X | n | A | Y | Ar |
|---|---|---|---|---|---|---|
| NO₂ | H | O | 0 | — | CONH₂ | 2,6-dichloro-4-(CF₃)phenyl |
| NO₂ | H | O | 0 | — | CON(CH₃)₂ | 2,6-dichloro-4-(CF₃)phenyl |
| NO₂ | H | O | 1 | —CH₂— | CONH₂ | 2,6-dichloro-4-(CF₃)phenyl |
| NO₂ | H | O | 1 | —CH₂— | CON(CH₃)₂ | 2,6-dichloro-4-(CF₃)phenyl |
| NO₂ | H | O | 1 | —CH(CH₃)— | CONH₂ | 2,6-dichloro-4-(CF₃)phenyl |
| NO₂ | H | O | 1 | —CH₂CH₂— | —CONH₂ | 2,6-dichloro-4-(CF₃)phenyl |
| NO₂ | H | O | 1 | —CH₂CH₂— | —CON(CH₃)₂ | 2,6-dichloro-4-(CF₃)phenyl |
| NO₂ | H | O | 1 | —CH(CH₃)—CH(CH₃)— | —CONH₂ | 2,6-dichloro-4-(CF₃)phenyl |

TABLE 1-continued (I)

$$\text{pyrazole structure with } R^1, R^2, Ar, C(=X)-(A)_n-Y$$

| R¹ | R² | X | n | A | Y | Ar |
|----|----|---|---|---|---|----|
| NO₂ | H | O | 1 | —CH₂CH₂— | —CONH₂ | 2,3,5-trichloro-4-CF₃-phenyl |
| NO₂ | H | O | 1 | —CH₂CH₂— | —CON(CH₃)₂ | 2,3,5-trichloro-4-CF₃-phenyl |
| NO₂ | H | O | 1 | —CH₂— | —CONH₂ | 2,3,5-trichloro-4-CF₃-phenyl |
| NO₂ | H | O | 1 | —CH(CH₃)— | CONH₂ | 2,3,5-trichloro-4-CF₃-phenyl |
| NO₂ | H | O | 1 | —CH₂— | CON(CH₃)₂ | 2,3,5-trichloro-4-CF₃-phenyl |
| NO₂ | CH₃ | O | 0 | — | COOCH₃ | 2,3,5-trichloro-4-CF₃-phenyl |
| NO₂ | CH₃ | O | 0 | — | COOC₂H₅ | 2,3,5-trichloro-4-CF₃-phenyl |
| NO₂ | CH₃ | O | 0 | — | COOH | 2,3,5-trichloro-4-CF₃-phenyl |

TABLE 1-continued

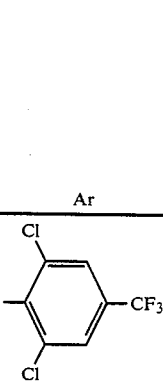

| R¹ | R² | X | n | A | Y | Ar |
|---|---|---|---|---|---|---|
| NO₂ | CH₃ | O | 1 | —CH₂— | COOC₂H₅ | (2,6-dichloro-4-trifluoromethyl-phenyl) |

If, for example, 5-amino-1-(2-bromo-4-trifluoromethyl-phenyl)-pyrazole and cyanoacetyl chloride are used as starting substances, the course of the reaction in process (a) according to the invention can be represented by the following equation:

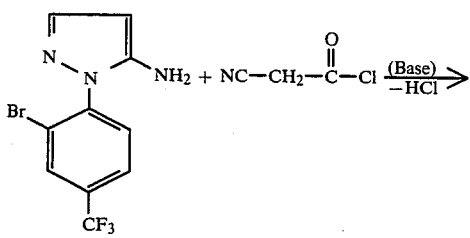

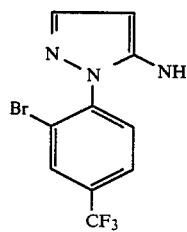

If, for example, 1-(2-chloro-4-trifluoromethoxy-phenyl)-5-ethoxaloyl-4-nitro-pyrazole and dimethyl sulphate are used as starting substances, the course of the reaction in process (b) according to the invention can be represented by the following equation:

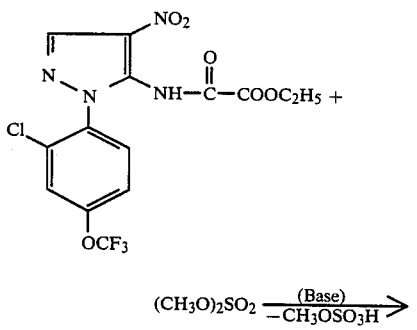

(CH₃O)₂SO₂ $\xrightarrow[-CH_3OSO_3H]{(Base)}$

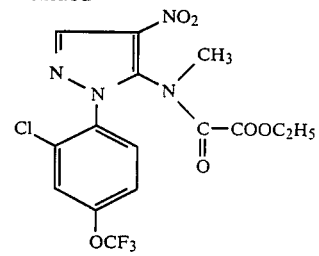

If, for example, 5-chloroacetylamino-4-nitro-1-(2,4,6-trichloro-phenyl)-pyrazole and tetrabutyl-ammonium cyanide are used as starting substances, the course of the reaction in process (c) according to the invention can be represented by the following equation:

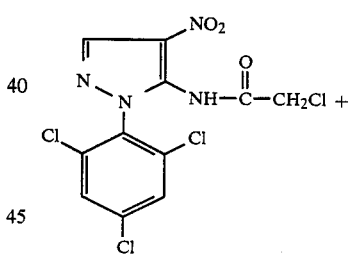

$(n\text{-}C_4H_9)_4\overset{\oplus}{N}\overset{\ominus}{CN} \xrightarrow{(n\text{-}C_4H_9)_4\overset{\oplus}{N}\overset{\ominus}{Cl}}$

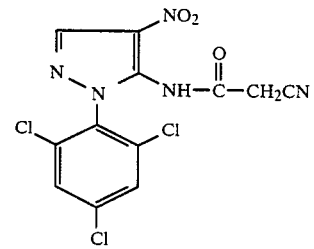

If, for example, 1-(2,4-dichloro-phenyl)-5-ethylmalonoyl-amino-pyrazole and nitric acid are used as starting substances, the course of the reaction in process (d) according to the invention can be represented by the following equation:

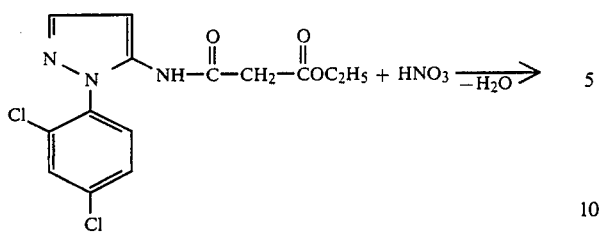 + HNO₃ $\xrightarrow{-H_2O}$

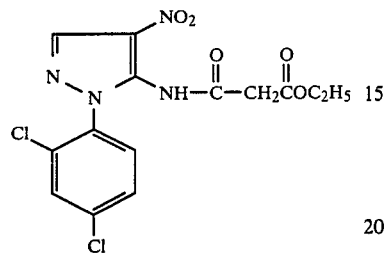

If, for example, 1-(2,6-dichloro-4-trifluoromethylthio-phenyl)-4-nitro-5-succinimido-pyrazole and ammonia are used as starting substances, the course of the reaction in process (e) according to the invention can be represented by the following equation:

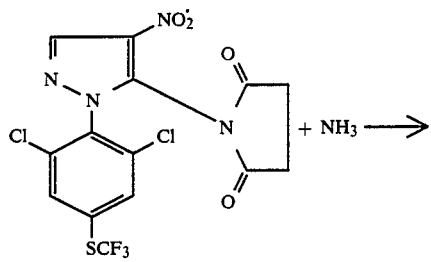 + NH₃ ⟶

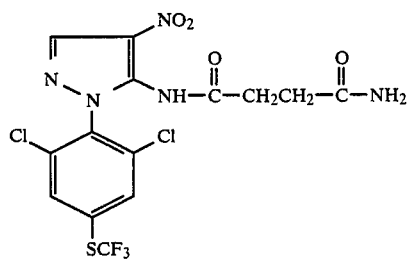

If, for example, 1-(2,4-dichloro-phenyl)-5-ethylmalonoyl-amino-pyrazole and sodium hydroxide are used as starting substances, the course of the reaction in process (f) according to the invention can be represented by the following equation:

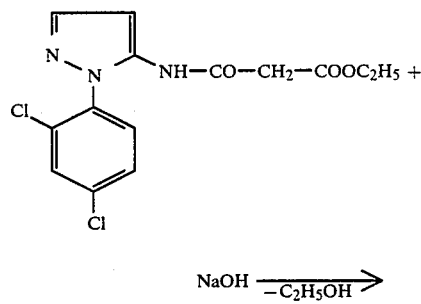

NaOH $\xrightarrow{-C_2H_5OH}$

-continued

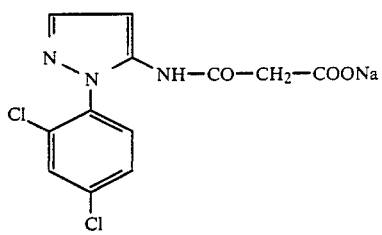

Formula (II) provides a general definition of the 5-amino-1-aryl-pyrazoles required as starting substances for carrying out process (a) according to the invention. In this formula (II), R¹ and Ar preferably represent those radicals which have already been mentioned as preferred for these radicals in connection with the description of the substances of the formula (I) according to the invention.

The 5-amino-1-aryl-pyrazoles of the formula (II) are known in some cases (compare, for example, DE-OS (German Published Specification) No. 3,402,308), and some of them are the subject of previous patent applications German Pat. No. 3,520,330 of June 7, 1985 and German Pat. No. 3,543,033 of Dec. 5, 1985, corresponding respectively to U.S. applications Ser. No. 866,638, filed May 22, 1986, now pending, and Ser. No. 934,067, filed Nov. 24, 1986, now pending and are obtainable by processes analogous to known processes (compare DE-OS (German Published Specification) No. 3,402,308, corresponding to U.S. Pat. No. 4,614,533)for example by a process in which arylhydrazines of the formula (X)

$$Ar-NH-NH_2 \quad (X)$$

in which

Ar has the abovementioned meaning, are either reacted in a 1st stage with 2-halogenoacrylonitriles of the formula (XI)

$$CH_2=C\begin{matrix}CN\\ \\Hal\end{matrix} \quad (XI)$$

in which

Hal represents halogen, in particular chlorine or bromine, if appropriate in the presence of a diluent, such as, for example, glacial acetic acid or ethanol, and if appropriate in the presence of a reaction auxiliary, such as, for example, sodium acetate, at temperatures between −20° C. and +20° C., to give the arylhydrazine derivatives of the formula (XII)

$$Ar-NH-NH-CH_2-CH\begin{matrix}CN\\ \\Hal\end{matrix} \quad (XII)$$

in which

Ar and Hal have the abovementioned meaning, and these are cyclized in a 2nd stage, if appropriate in the presence of a diluent, such as, for example, ethylene glycol monoethyl ether, and if appropriate in the presence of an acid catalyst, such as, for example, sulphuric acid or phosphoric acid, at temperatures between +50°

C. and +150° C., or are cyclized directly in one reaction step, without isolation of the intermediate stage of the formula (XII), if appropriate in the presence of a diluent, such as, for example, ethylene glycol monoethyl ether or ethanol, at temperatures between +50° C. and +150° C., and the 4-unsubstituted 5-amino-1-aryl-pyrazoles thus obtainable, of the formula (IIa)

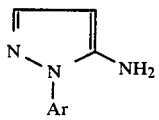
(IIa)

in which

Ar has the abovementioned meaning, are nitrated in a secondary reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C., or alternatively are halogenated with a halogenating agent, such as, for example, chlorine, sulphuryl chloride, phosphorus pentachloride, N-chlorosuccinimide, bromine, phosphorus tribromide or N-bromosuccinimide, if appropriate in the presence of a diluent, such as, for example, methylene chloride or glacial acetic acid, and if appropriate in the presence of a reaction auxiliary, such as, for example, boron trifluoride, at temperatures between −20° C. and +50° C.

It may thereby be of advantage, if appropriate, for the amino group in the 5-position of the pyrazole ring to be protected with the aid of the customary protective group technique, for example by acylation, before the halogenation or nitration reaction and for the amino-protective group to be split off again after the halogenation or nitration, likewise in the customary manner, for example by hydrolysis with an aqueous or alcoholic base.

The arylhydrazines (X) are known (compare, for example, U.S. Pat. Nos. 4,127,575; 3,609,158; DE-OS (German Published Specification) No. 2,558,399; and J. Chem. Soc. C. 1971, 167–174), or they can be obtained by known processes in a simple analogous manner (compare, for example, Houben-Weyl "Methoden der organischen Chemie" ("Methods of Organic Chemistry") Volume X/2, page 203, Thieme Verlag Stuttgart 1967; and DE-OS (German Published Specification) No. 3,402,308).

The halogenoacrylonitriles of the formula (XI) are generally known compounds of organic chemistry.

Formula (III) provides a general definition of the acylating agents furthermore required as starting substances for carrying out process (a) according to the invention. In this formula (III), X, Y, A and the index n preferably have those meanings which have already been mentioned as preferred for these substituents in connection with the description of the substances of the formula (I) according to the invention.

$E^1$ preferably represents halogen, in particular chlorine or bromine, or represents a

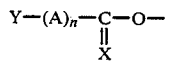

radical, X, Y, A and the index n having the abovementioned meanings. The acylating agents of the formula (III) are generally known compounds of organic chemistry.

Formula (Ia) provides a general definition of the 5-acylamino-pyrazole derivatives required as starting substances for carrying out process (b) according to the invention. In this formula (Ia), $R^1$, X, Y, A, the index n and Ar preferably have those meanings which have already been mentioned as preferred for these substituents in connection with the description of the substances of the formula (I) according to the invention.

The 5-acylamino-pyrazole derivatives of the formula (Ia) are compounds according to the invention and are obtainable with the aid of processes (a), (c), (d) or (e) according to the invention.

Formula (IV) provides a general definition of the alkylating agents furthermore required as starting substances for carrying out process (b) according to the invention. In this formula (IV), $R^{2-1}$ preferably represents straight-chain or branched alkyl with 1 to 12 carbon atoms, in particular methyl, ethyl, n- or i-propyl or n-, i-, s- or t-butyl; or furthermore represents alkenyl or alkinyl with in each case 3 to 6 carbon atoms, in particular allyl or propargyl, or represents cycloalkyl with 3 to 6 carbon atoms, in particular cyclopropyl, cyclopentyl or cyclohexyl. $E^2$ preferably represents chlorine, bromine or iodine, or represents methoxysulphonyloxy, or represents p-toluenesulphonyloxy.

The alkylating agents of the formula (IV) are generally known compounds of organic chemistry.

Formula (V) provides a general definition of the 5-acylamido-1-aryl-pyrazoles required as starting substances for carrying out process (c) according to the invention. In this formula (V), $R^1$, $R^2$, X, A, Ar and the index n preferably have those meanings which have already been mentioned as preferred for these substituents in connection with the description of the substances of the formula (I) according to the invention. $E^3$ preferably represents chlorine or bromine.

The 5-acylamido-1-aryl-pyrazoles of the formula (V) are known (compare U.S. Pat. No. 4,363,804 or DE-OS (German Published Specification) No. 3,402,308, corresponding to U.S. Pat. No. 4,614,533), or they are the subject of previous patent application German Patent No. 3,520,330, corresponding to U.S. Ser. No. 866,638, supra, and are obtainable by processes analogous to known processes (compare, for example, DE-OS German Published Specification) No. 3,402,308, corresponding to U.S. Pat. No. 4,614,533; compare also the Preparation Examples), for example by a process in which 5-amino-1-arylpyrazoles of the formula (II)

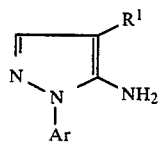
(II)

in which $R^1$ and Ar have the abovementioned meaning, are acylated with acylating agents of the formula (XIII)

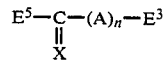
(XIII)

in which
E³, X, A and the index n have the abovementioned meaning and
E⁵ represents a leaving group, such as, for example, halogen, in particular chlorine or bromine, or represents an

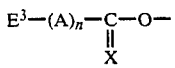

radical,
wherein
E³, A, X and the index n have the abovementioned meaning, if appropriate in the presence of a diluent, such as, for example, methylene chloride, and if appropriate in the presence of an acid-binding agent, such as, for example, pyridine, at temperatures between −20° C. and +120° C., and, if appropriate, the products are subsequently alkylated in a 2nd stage by processes analogous to known processes and by a process analogous to process (b) according to the invention with alkylating agents of the formula (IV)

 (IV)

in which
E² and R²⁻¹ have the abovementioned meaning, if appropriate in the presence of a diluent, such as, for example, acetonitrile, and if appropriate in the presence of a catalyst, such as, for example, sodium methylate, at temperatures between 0° C. and 80° C.

The acylating agents of the formula (XIII) are generally known compounds of organic chemistry.

Formula (VI) provides a general definition of the cyano derivatives furthermore required as starting substances for carrying out process (c) according to the invention. In this formula (VI), W preferably represents hydrogen, or represents a sodium or potassium cation, or represents a tetrabutylammonium cation.

The cyano derivatives of the formula (VI) are generally known compounds of organic chemistry.

Formula (Ie) provides a general definition of the 5-acylamino-pyrazole derivatives required as starting substances for carrying out process (d) according to the invention. In this formula (Ie), R², X, Y, A, Ar and the index n preferably have those meanings which have already been mentioned as preferred for these substituents in connection with the description of the substances of the formula (I) according to the invention.

The 5-acylamino-pyrazole derivatives of the formula (Ie) are compounds according to the invention and are obtainable with the aid of processes (a), (b), (c), (e) or (f) according to the invention.

Formula (VII) provides a general definition of the halogenating or nitrating agents furthermore required as starting substances for carrying out process (d) according to the invention. In this formula (VII), R¹⁻¹ preferably represents chlorine, bromine or nitro.

E⁴ preferably represents a customary leaving group, such as, for example, halogen or phosphorus- or sulphur-containing halogenated leaving groups. Suitable halogenating and nitrating agents are, for example, nitric acid, nitrating acid, sulphuryl chloride, phosphorus oxychloride, phosphorus oxybromide, phosphorus tribromide and similar generally customary halogenating and nitrating agents.

The halogenating and nitrating agents of the formula (VII) are generally known compounds.

Formula (VIII) provides a general definition of the 5-imido-pyrazoles required as starting substances for carrying out process (e) according to the invention. In this formula (VIII), R¹ and Ar preferably or particularly preferably represent those radicals which have already been mentioned as preferred or particularly preferred for these substituents in connection with the description of the substances of the formula (I) according to the invention.

A¹ preferably represents the alkylene chains

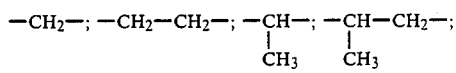

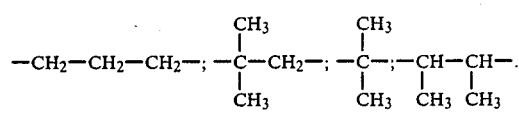

The 5-imido-pyrazoles of the formula (VIII) are not yet known; however, they can be obtained in the customary manner, by a process in which 5-amino-1-aryl-pyrazoles of the formula (II)

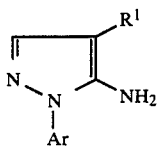 (II)

in which
R¹ and Ar have the abovementioned meaning, are reacted with cyclic dicarboxylic acid anhydrides of the formula (XIV)

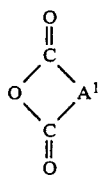 (XIV)

in which
A¹ has the abovementioned meaning, if appropriate in the presence of a diluent and if appropriate in the presence of an acid catalyst, and if appropriate in the presence of dehydrating reagents, it also being possible, depending on the reaction conditions, for the open-chain amide acids of the formula (Ig)

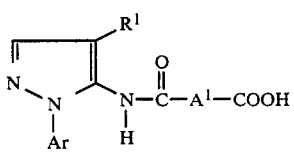 (Ig)

in which
R¹, A¹ and Ar have the abovementioned meaning, to be isolated, these then being cyclized in a second reaction step under dehydrating conditions with the addition of a reaction auxiliary or a catalyst, such as, for example, dicylohexylcarbodiimide, trifluoroacetic anhydride or p-toluenesulphonic acid, to give the 5-imidopyrazoles of the formula (VIII).

Possible diluents for the preparation of the 5-imidopyrazoles of the formula (VIII) are inert organic solvents. The organic solvents mentioned in the case of process (a) according to the invention are preferably used here. Water-immiscible organic solvents, such as toluene, chlorobenzene and carbon tetrachloride, or organic acids, such as acetic acid and propionic acid, are particularly preferred.

If appropriate, the preparation of the 5-imidopyrazoles of the formula (VIII) is carried out using acid catalysts, such as mineral acids, carboxylic acids and sulphonic acids, and in the presence of dehydrating reagents, such as dicyclohexylcarbodiimide or acid anhydrides and acid chlorides, such as phosphorus pentoxide, phosphorus oxychloride, thionyl chloride and trifluoroacetic anhydride.

The temperatures can be varied within a substantial range in the process for the preparation of the 5-imidopyrazoles of the formula (VIII). The reaction is in general carried out at temperatures between 20° C. and 180° C., preferably between 50° C. and 180° C.

For carrying out the process for the preparation of the 5-imido-pyrazoles of the formula (VIII), 1 to 2 mols, preferably 1 to 1.2 mols, of dicarboxylic acid anhydride of the formula (XIV), 0.01 to 1 mol of acid catalyst and 1 to 15 mols, preferably 1 to 10 mols, of dehydrating reagent are employed per mol of 5-amino-1-arylpyrazole of the formula (II).

The reaction is carried out and the 5-imido-pyrazoles of the formula (VIII) are worked up and isolated in the generally customary manner.

The 5-imido-pyrazoles of the formula (VIII) are not only interesting intermediate products but also exhibit good herbicidal and plant growth-regulating properties when applied in appropriate amounts.

Formula (IX) provides a general definition of the nucleophilic compounds furthermore required as starting substances for carrying out process (e) according to the invention. In this formula, $R^3$ preferably represents those radicals which have already been mentioned as preferred for this substituent in connection with the description of the substances of the formula (I) according to the invention.

The nucleophilic compounds of the formula (IX) are generally known compounds of organic chemistry.

Formula (Ih) provides a general definition of the 5-acylamino-pyrazole derivatives required as starting substances for carrying out process (f) according to the invention. In this formula (Ih), $R^1$, $R^2$, X, $X^1$, A, Ar and the index n preferably have those meanings which have already been mentioned as preferred for these substituents in connection with the description of the substances of the formula (I) according to the invention.

$R^{3-1}$ preferably represents hydroxyl, methoxy, ethoxy or n- or i-propoxy. The compounds of the formula (Ih) are substances according to the invention and are obtainable with the aid of processes (a), (b), (d) or (e) according to the invention.

Possible diluents for carrying out process (a) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, process (a) according to the invention is carried out in the presence of a suitable acid-binding agent.

Possible acid-binding agents are all the customary inorganic or organic bases. These include, for example, alkali metal hydroxides, such as sodium hydroxdide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

If appropriate, process (a) according to the invention can also be carried out in the presence of a suitable acylation catalyst. Acylation catalysts which are used are, preferably, proton acids, such as sulphuric acid, hydrochloric acid, phosphoric acid or trifluoroacetic acid, or Lewis acids, such as aluminum trichloride, boron trifluoride or iron trichloride.

The reaction temperatures can be varied within a substantial range in carrying out process (a) according to the invention. The reaction is in general carried out at temperatures between $-20°$ C. and $+150°$ C., preferably at temperatures between 0° C. and 100° C.

For carrying out process (a) according to the invention, in general 1.0 to 15.0 mol, preferably 1.0 to 5.0 mol, of acylating agent of the formula (III), if appropriate 1.0 to 3.0 mol, preferably 1.0 to 2.0 mol, of acid-binding agent or if appropriate 0.1 to 3.0 mol, preferably 0.1 to 2.0 mols, of acylation catalyst are employed per mol of 5-amino-1-aryl-pyrazole of the formula (II). The reaction is carried out and the reaction products of the formula (Ia) are worked up and isolated by customary known methods.

Possible diluents for carrying out process (b) according to the invention are likewise inert organic solvents. The organic solvents mentioned in the case of process (a) are preferably used.

If appropriate, process (b) according to the invention can also be carried out in a two-phase system, such as, for example, water/toluene or water/methylene chloride, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzylammonium methylsulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride.

Possible acid-binding agents for carrying out preparation process (b) are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out process (b) according to the invention. The reaction is in general carried out at temperatures between −20° C. and +150° C., preferably at temperatures between 0° C. and +100° C.

For carrying out process (b) according to the invention, in general 1.0 to 20.0 mols, preferably 1.0 to 15.0 mols, of alkylating agent of the formula (IV) and if appropriate 1.0 to 3.0 mols, preferably 1.0 to 2.0 mols, of acid-binding agent and 0.01 to 1.0 mol of phase transfer catalyst are employed per mol of 5-acylamino-pyrazole derivatives of the formula (Ia). The reaction is carried out and the reaction products of the formula (Ib) are worked up and isolated in the generally customary manner.

Possible diluents for carrying out process (c) according to the invention are inert organic solvents or aqueous systems. The organic solvents mentioned in the case of process (a) are preferably used. Polar organic solvents, such as methanol, ethanol, n-propanol, i-propanol, n-butanol, i-butanol, t-butanol, ethylene glycol, diethylene glycol, ethylene glycol monomethyl ether or monoethyl ether, diethylene glycol monoethyl ether or monoethyl ether, mixtures thereof with water or pure water are moreover preferred diluents.

If appropriate, process (c) according to the invention is carried out in the presence of a suitable acid-binding agent. Possible acid-binding agents are all the inorganic or organic bases which can usually be employed. The bases listed in the case of process (b) are preferably used as acid-binding agents.

A particularly preferred embodiment of process (c) comprises a procedure in which alkali metal, alkaline earth metal or tetraalkylammonium salts of hydrocyanic acid are reacted either in inert organic solvents or in a two-phase system, such as, for example, water/toluene or water/methylene chloride, if appropriate in the presence of a phase transfer catalyst. The catalysts mentioned in the case of process (b) are preferably used.

The reaction temperatures can be varied within a substantial range in carrying out process (c) according to the invention. The reaction is in general carried out at temperatures between −20° C. and +120° C., preferably at temperatures between 0° C. and 100° C.

For carrying out process (c) according to the invention, in general 1.0 to 5.0 mols, preferably 1.0 to 3.0 mols, of cyano derivative of the formula (VI) and if appropriate 1.0 to 5.0 mols, preferably 1.0 to 3.0 mols, of acid-binding agent or 0.001 to 2.0 mols, preferably 0.01 to 1.0 mol, of phase transfer catalyst are employed per mol of 5-acylamido-1-aryl-pyrazole of the formula (V). The reaction is carried out and the reaction products of the formula (Ia) are worked up and isolated by processes analogous to generally known processes.

Possible diluents for carrying out preparation process (d) are all the solvents which can usually be employed for such electrophilic replacements. The acids or mixtures suitable as reagents, such as, for example, nitric acid, nitrating acid, sulphuryl chloride or nitrating acid, are preferably used simultaneously as the diluent. If appropriate, inert organic solvents, such as, for example, glacial acetic acid or chlorinated hydrocarbons, such as methylene chloride, chloroform or carbon tetrachloride, are also possible diluents.

Possible catalysts or reaction auxiliaries for carrying out preparation process (d) are likewise the catalysts customary for such reactions; acid catalysts, such as, for example, sulphuric acid, iron-III chloride or other Lewis acids, or acetic anhydride are preferably used.

The reaction temperatures can be varied within a substantial range in carrying out preparation process (d). The reaction is in general carried out between −50° C. and +200° C., preferably between −20° C. and +150° C.

For carrying out preparation process (d), in general 1.0 to 10.0 mols, preferably 1.0 to 5.0 mols, of halogenating or nitrating agent of the formula (VII) and if appropriate 0.1 to 10 mol of catalyst or reaction auxiliary are employed per mol of 5-acylamino-pyrazole derivative of the formula (Ie). The reaction is carried out and the reaction products of the formula (Id) are worked up and isolated in the generally customary manner.

Possible diluents for carrying out preparation process (e) are inert organic solvents or aqueous systems. The organic solvents mentioned in the case of process (a) are preferably used. The reaction can also be carried out in an excess of the nucleophilic compound (IX) as the solvent.

If appropriate, process (e) according to the invention is carried out in the presence of an acid-binding agent. Possible acid-binding agents are all the customary inorganic or organic bases, such as those already mentioned in particular in the case of process (a).

A preferred embodiment of process (e) comprises a procedure in which the nucleophilic compounds of the formula (IX) are employed in the form of their salts.

Possible salts here are, in particular, the alkali metal, alkaline earth metal and ammonium salts of the compounds of the formula (IX).

The reaction temperatures can be varied within a substantial range in carrying out process (e) according to the invention. The reaction is in general carried out at temperatures between 0° C. and 180° C., preferably at temperatures between 20° C. and 150° C.

For carrying out process (e) according to the invention, in general 1 to 15 mols, preferably 1 to 5 mols, of nucleophilic compound of the formula (IX), if appropriate 1 to 3 mols, preferably 1 to 2 mols, of acid-binding agent or if appropriate 1 to 3 mols, preferably 1 to 2 mols, of salt of the compound of the formula (IX) are employed per mol of 5-imino-pyrazole of the formula (VIII). The reaction is carried out and the reaction products of the formula (If) are worked up and isolated by customary known methods.

Possible diluents for carrying out process (f) according to the invention are inert organic solvents. The organic solvents mentioned in the case of process (a) are preferably used. However, aqueous or aqueous-organic systems can also preferably be used as the diluent.

Possible salt-forming agents are all the inorganic or organic bases which can usually be employed. Examples of such bases are: sodium hydroxide, potassium hydroxide, lithium hydroxide, calcium hydroxide, barium hydroxide and magnesium hydroxide and sodium carbonate, potassium carbonate and calcium carbonate; sodium bicarbonate, potassium bicarbonate, sodium methylate, triethylamine, isopropylamine and dimethylbenzylamine.

The reaction temperatures can be varied within a substantial range in carrying out process (f) according to the invention. The reaction is in general carried out at temperatures between 0° C. and 80° C., preferably at temperatures between 20° C. and 50° C.

For carrying out process (f) according to the invention, in general 1 to 5 mols, preferably 1 to 2 mols, of inorganic or organic base are employed per mol of 5-acylamino-pyrazole derivative of the formula (Ih). The reaction is carried out and the reaction products of the formula (Ig) are worked up and isolated in the generally customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating monocotyledon and dicotyledon weeds in monocotyledon and dicotyledon crops, such as, for example, wheat or cotton.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soy beans or cereals. Using growth regulators it is also possible, for example, to inhibit the degradation of desired constituents, such as, for example, sugar in sugar beets or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance, the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the forces required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, wettable powders, suspensions, powders, dusting agents, foams, pastes, soluble powders, granules, suspension-emulsion concentrates, natural and synthetic materials impregnated with active compound, aerosols, very fine capsules in polymeric substances and in coating compositions for use on seed, as well as ULV formulations.

These formulations are produced in known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkylsulphonates, alkylsulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phosbholipids, such as cephalins and lecithins, and synthetic phosspholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When employed as herbicides, the active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beets and 4-amino-6-(1,1-dimethylethyl)-3-methylthio-1,2,4-triazin-5(4H)-one for combating weeds in soy beans.

Mixtures with N,N-dimethyl-N'-(3-trifluoromethylphenyl)-urea; N,N-dimethyl-N'-(4-isopropylphenyl)-urea; 2,4-dichlorophenoxyacetic acid; 2,4-dichlorophenoxypropionic acid; (2-methyl-4-chlorophenoxy)-acetic acid; (4-chloro-2-methylphenoxy)-propionic acid; chloroacetic acid N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; methyl 5-(2,4-dichlorophenoxy)-2-nitrobenzoate; 3,5-diiodo-4-hydroxybenzonitrile; 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; 4-ethylamino-2-t-butylamino-6-methylthio-s-triazine; N-methyl-2-(1,3-benzothiazol-2-yloxy)-acetanilide; exo-1-methyl-4-(1-methylethyl)-2-(2-methylphenyl-methoxy)7-oxabicyclo-(2,2,1)-heptane; S-(2,3,3-trichloroallyl) N,N-di-isopropyl-thiolcarbamate; N-(1-ethylpropyl)-3,4-dimethyl-2,6-dinitroaniline; 1-methyl-3-phenyl-5-(3-trifluoromethylphenyl)-4-pyridone; 2-[5-methyl-5-(1-methylethyl)-4-oxo-2-imidazolin-2-yl]-3-quinolinecarboxylic acic; [(4-amino-3,5-dichloro-6-fluoro-2-pyridinyl)-oxy]-acetic acid; and 3,5-dibromo-4-hydroxy-benzonitrile is also possible.

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

When used by the post-emergence method, the compounds according to the invention can be applied by themselves or in combination with emulsifiable oils, surface-active substances and other additives.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

In the treatment of parts of plants, the active compound concentrations in the use forms can be varied within a substantial range. They are in general between 1 and 0.0001% by weight, preferably between 0.5 and 0.001%.

In the treatment of seed, active compound amounts of 0.001 to 50 g per kilogram of seed, preferably 0.01 to 10 g, are in general required.

In the treatment of soil, active compound concentrations of 0.00001 to 0.1% by weight, preferably 0.0001 to 0.02%, are required at the place of action.

The amounts applied can be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

The preparation and use of the active compounds according to the invention can be seen from the following examples:

PREPARATION EXAMPLES

EXAMPLE 1

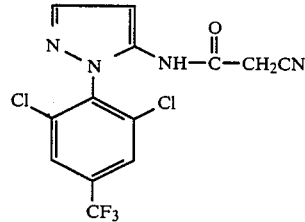

(Process a)

22.5 g (0.076 mol) of 5-amino-1-(2,6-dichloro-4-trifluoromethylphenyl)-pyrazole and 8 g (0.1 mol) of pyridine are taken in 200 ml of acetonitrile, and 13.2 g (0.128 mol) of cyanoacetyl chloride are added dropwise at 20°–25° C., while stirring and cooling. The reaction mixture is stirred at room temperature for a further two hours and then poured into water. After extraction with methylene chloride and drying of the organic phase over sodium sulphate, the solvent is distilled off in vacuo. The crystalline residue is stirred with a mixture of ligroin and diisopropyl ether and filtered off with suction.

22 g (80% of theory) of 5-cyanoacetylamino-1-(2,6-dichloro-4-trifluoromethyl-phenyl)-pyrazole of melting point 169°175° C. are obtained.

EXAMPLE 2

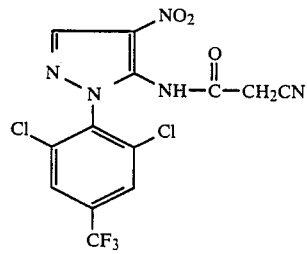

(Process d)

7.26 g (0.02 mol) of 5-cyanoacetylamino-1-(2,6-dichloro-4-trifluoromethyl-phenyl)-pyrazole (Example 1) are taken in 70 ml of glacial acetic acid, and 2 ml of acetic anhydride and 2 ml of nitric acid are added dropwise in succession at about 10° C. A crystalline solid precipitates out of the initially clear solution after prolonged stirring. After filtration with suction, washing several times with diisopropyl ether and drying, 2.9 g (36% of theory) of 5-cyanoacetylamino-1-(2,6-dichloro-4-trifluoromethyl-phenyl)-4-nitro-pyrazole of melting point 221°-223° C. are obtained.

EXAMPLE 3

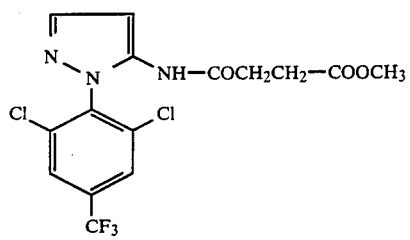

(a)

(Process e)

1.3 g (0.024 mol) of sodium methylate are added to a solution of 8.25 g (0.0218 mol) of 1-(2,6-dichloro-4-trifluoromethyl-phenyl)-5-succinimido-pyrazole in 50 ml of anhydrous methanol at room temperature and the mixture is stirred for 18 hours. Thereafter, the reaction mixture is poured onto 200 ml of 2% strength ammonium chloride solution and 150 ml of methylene chloride. The organic phase is separated off, washed with water and sodium chloride solution, dried over magnesium sulphate and freed from the solvent in vacuo.

7.0 g (78.3% of theory) of 1-(2,6-dichloro-4-trifluoromethyl-phenyl)-5-(2-methoxycarbonylpropionylamido)-pyrazole of melting point 127°-132° C. are obtained.

(b) Preparation of the Starting Substance

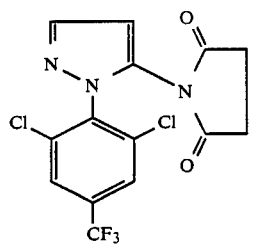

(VIII-1)

42 g (0.42 mol) of succinic anhydride and 40.8 g (0.404 mol) of triethylamine are added in succession to a solution of 20 g (0.0676 mol) of 5-amino-1-(2,6-dichloro-4-trifluoromethyl-phenyl)-pyrazole in 150 ml of acetonitrile and the mixture is warmed at 80° C. for 16 hours. The solvent is removed in vacuo and the residue is taken up in water. The precipitate formed is filtered off, rinsed with water and dried.

21.6 (84.5% of theory) of 1-(2-6-dichloro-4-trifluoromethyl-phenyl)-5-succinimido-pyrazole of melting point 162°-165° C. are obtained.

EXAMPLE 4

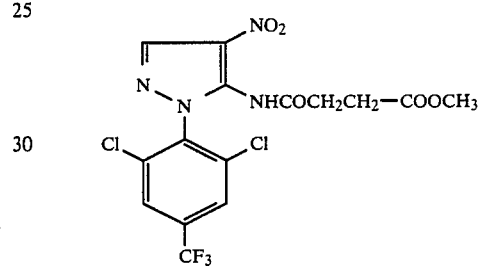

(Process d)

1.2 ml (0.013 mol) of acetic anhydride and 0.5 ml (0.012 mol) of 99% strength nitric acid are added to a solution of 4.1 g (0.01 mol) of 1-(2,6-dichloro-4-trifluoromethyl-phenyl)-5-(2-methoxycarbonyl-propionylamido)-pyrozole in 30 ml of glacial acetic acid at 15°-20° C. The mixture is stirred at room temperature for 14 hours. Thereafter, the reaction solution is poured onto 100 ml of water. The precipitate is filtered off, washed neutral with water and dried in vacuo.

4.1 g (90% of theory) of 1-(2,6-dichloro-4-trifluoromethyl-phenyl)-5-(2-methoxycarbonyl-propionylamido)-4-nitro-pyrazole of melting point 149°-151° C. are obtained.

The following 5-acylamino-pyrazole derivatives of the general formula (I) are obtained in a corresponding manner and in accordance with the general preparation statements:

TABLE 2

$$(I)$$

Structure: Pyrazole with N-Ar, N-C(=X)-(A)ₙ-Y, R¹ at 4-position, R² on N

| Example No. | R¹ | R² | $-\overset{X}{\underset{\|}{C}}-(A)_n-Y$ | Ar | Melting point (°C.) |
|---|---|---|---|---|---|
| 5 | H | H | —CO—CH₂—CO—OC₂H₅ | 2,6-Cl₂-4-CF₃-phenyl | 104–06 |
| 6 | NO₂ | H | —CO—CH₂—CO—OC₂H₅ | 2,6-Cl₂-4-CF₃-phenyl | 107–10 |
| 7 | H | H | —CO—CH(CH₃)—CO—OC₂H₅ | 2,6-Cl₂-4-CF₃-phenyl | 115–16 |
| 8 | NO₂ | H | —CO—CH(CH₃)—CO—OC₂H₅ | 2,6-Cl₂-4-CF₃-phenyl | 120–24 |
| 9 | NO₂ | H | —CO—CO—OH | 2,6-Cl₂-4-CF₃-phenyl | 211–15 |
| 10 | H | H | —CO—COOC₂H₅ | 2,6-Cl₂-4-CF₃-phenyl | 119–24 |
| 11 | H | H | —CO—CO—OC₂H₅ | 2,3-Cl₂-4-CF₃-phenyl | 109–16 |

TABLE 2-continued

Structure (I):

Pyrazole core with N-Ar, N(R²)-C(=X)-(A)ₙ-Y, and R¹ substituent.

| Example No. | R¹ | R² | $-\underset{X}{\overset{\parallel}{C}}-(A)_n-Y$ | Ar | Melting point (°C.) |
|---|---|---|---|---|---|
| 12 | H | H | —CO—CO—OC₂H₅ | 2,6-Cl₂-4-SO₂CF₃-phenyl | 103-1 |
| 13 | NO₂ | H | —CO—CO—OC₂H₅ | 2,6-Cl₂-4-CF₃-phenyl | 127-3 |
| 14 | NO₂ | H | —CO—CO—ONa | 2,6-Cl₂-4-CF₃-phenyl | 228-3 |
| 16 | NO₂ | H | —CO—CH(CH₃)—CO—O—C₂H₅ | 2,3,6-Cl₃-4-CF₃-phenyl | 108-12 |
| 17 | NO₂ | H | —CO—COOH | 2,3,6-Cl₃-4-CF₃-phenyl | 178-80 |
| 18 | NO₂ | H | —CO—COOC₂H₅ | 2,3,6-Cl₃-4-CF₃-phenyl | 117-119 |
| 19 | NO₂ | H | —CO—COOC₂H₅ | 2,6-Cl₂-4-SO₂CF₃-phenyl | 138-140 |

TABLE 2-continued
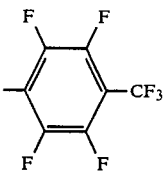
(I)
| Example No. | R¹ | R² | $-\overset{X}{\underset{\parallel}{C}}-(A)_n-Y$ | Ar | Melting point (°C.) |
|---|---|---|---|---|---|
| 20 | H | H | —CO—COOC₂H₅ | 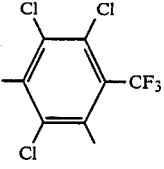 | 85–86 |
| 21 | NO₂ | H | —CO—COONa | 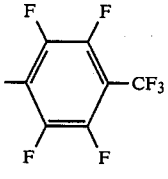 | 175–182 |
| 22 | NO₂ | | —CO—COOC₂H₅ | 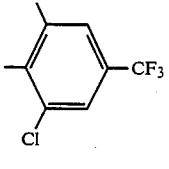 | 136–138 |
| 23 | NO₂ | H | —CO—CH₂—CH₂—COOH | 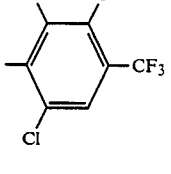 | 176–180 |
| 24 | H | H | —CO—COOC₂H₅ | 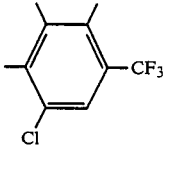 | 104–108 |
| 25 | NO₂ | H | —CO—COOC₂H₅ | 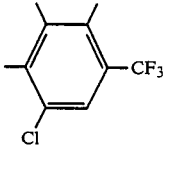 | 124–128 |
| 26 | NO₂ | H | —CO—COOH | 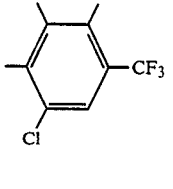 | 193 |

TABLE 2-continued
$$\text{(I)}$$
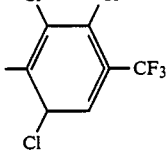
| Example No. | R¹ | R² | $\overset{X}{\underset{\|}{-C}}-(A)_n-Y$ | Ar | Melting point (°C.) |
|---|---|---|---|---|---|
| 27 | NO₂ | H | —CO—CH₂—COOC₂H₅ | 2,6-Cl₂-4-Cl-3-CF₃ phenyl | 108–109 |
| 28 | H | H | CO—CH₂—CN | 2,3,5,6-F₄-4-CF₃ phenyl | 142–145 |
| 29 | H | H | —CO—CH₂—CN | 3,5-Cl₂-4-SO₂CF₃ phenyl | 155–158 |
| 30 | H | H | —CO—CH₂—CN | 2-Cl,3-F,5-Cl,4-CF₃ phenyl | 174–179 |
| 31 | H | H | CO—CH₂—CN | 2-Cl,3-F,5-Cl,6-F,4-CF₃ phenyl | 194–201 |
| 32 | H | H | —CO—CH₂—CN | 2,3,5-Cl₃-4-CF₃ phenyl | 147–155 |
| 33 | NO₂ | H | —CO—CH₂—CN | 2,3,5,6-F₄-4-CF₃ phenyl | 148–155 |

TABLE 2-continued (I) Structure: pyrazole with R¹ at 4-position, N-R² and N-Ar, C(=X)-(A)ₙ-Y substituent

| Example No. | R¹ | R² | $-\overset{X}{\underset{\|}{C}}-(A)_n-Y$ | Ar | Melting point (°C.) |
|---|---|---|---|---|---|
| 34 | NO₂ | H | —CO—CH₂—CN | 2,6-dichloro-4-(SO₂CF₃)phenyl | 183–187 |
| 35 | NO₂ | H | —CO—CH₂—CN | 2,6-dichloro-3-fluoro-4-CF₃phenyl | 180–190 |
| 36 | NO₂ | H | —CO—CH₂—CN | 2,6-dichloro-3,5-difluoro-4-CF₃phenyl | 180–190 |
| 37 | NO₂ | H | —CO—CH₂—COOCH₃ | 2,3,6-trichloro-4-CF₃phenyl | 163–164 |
| 38 | NO₂ | H | —CO—CH₂—COOCH₃ | 2,3,6-trichloro-4-CF₃phenyl | 163–164 |
| 39 | NO₂ | H | —CO—CH₂—CH₂—COOH | 2,3,6-trichloro-4-CF₃phenyl | 204–206 |
| 40 | NO₂ | H | —CO—CH₂—CH₂—COOH | 2,3,5,6-tetrafluoro-4-CF₃phenyl | 146–148 |

TABLE 2-continued (I)

Structure: pyrazole with R¹ at 4-position, N-R² and N-Ar substituents, with -C(X)-(A)ₙ-Y group

| Example No. | R¹ | R² | -C(X)-(A)ₙ-Y | Ar | Melting point (°C.) |
|---|---|---|---|---|---|
| 41 | NO₂ | H | —CO—CH₂—CH₂—COOH | 2-Cl, 3-F, 4-CF₃, 6-Cl phenyl | 175–178 |
| 42 | NO₂ | H | —CO—CH₂—CH₂—COOH | 3-F, 4-CF₃, 5-Cl phenyl | 177–180 |
| 43 | NO₂ | H | —CO—CH₂—CH₂—COOH | 2-Cl, 3-F, 4-CF₃ phenyl | 112–114 |

The following starting compounds of the general formula (VIII) are obtained according to Example 3b and in accordance with the general preparation statements:

TABLE 3

(VIII)

Structure: pyrazole with R¹ at 4-position, N-Ar, and cyclic imide (succinimide-type) with A¹ linker

| Compound No. | R¹ | A¹ | Ar | Melting point (°C.) |
|---|---|---|---|---|
| VIII-2 | NO₂ | —CH₂CH₂— | 2-Cl, 4-CF₃, 6-Cl phenyl | 152–54 |
| VIII-3 | NO₂ | —CH₂CH₂— | 2-Cl, 3-Cl, 4-CF₃, 6-Cl phenyl | 174–75 |
| VIII-4 | NO₂ | —CH₂CH₂— | 2,3,5,6-tetrafluoro-4-CF₃ phenyl | 163–67 |
| VIII-5 | NO₂ | —CH₂CH₂— | 2-Cl, 3-F, 4-CF₃, 6-Cl phenyl | 128–130 |
| VIII-6 | NO₂ | —CH₂CH₂— | 3-F, 4-CF₃, 5-Cl phenyl | 138–140 |

TABLE 3-continued

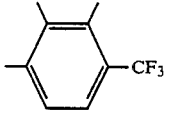

| Compound No. | R¹ | A¹ | Ar | Melting point (°C.) |
|---|---|---|---|---|
| VIII-7 | $NO_2$ | $-CH_2CH_2-$ | 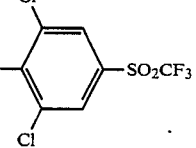 | 168–171 |
| VIII-8 | $NO_2$ | $-CH_2CH_2-$ | 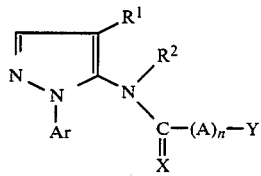 | 242–254 |

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient here to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, a clearly superior activity and crop plant selectivity compared with comparison substance (A) are shown, for example, by the compounds according to preparation Examples 2, 6, 8, 13 and 14.

EXAMPLE B

Post-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, a clearly superior activity and crop plant selectivity compared with comparison substance (A) are shown, for example, by the compounds according to preparation Examples 2, 4, 5, 6, 7, 8, 9, 13 and 14.

EXAMPLE C

Defoliation and Desiccation of the Leaves of Cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

In this test, the compounds according to preparation Examples 2, 6, 7, 8 and 14 show a clear superiority in comparison with the untreated control.

It will be understood that the specification and examples are illustrative but not limitative of the present invention and that other embodiments within the spirit and scope of the invention will suggest themselves to those skilled in the art.

We claim:

1. A 5-acylamino-pyrazole derivative of the formula in which
R¹ represents hydrogen, nitro, flourine, chlorine, bromine or iodine;
R² represents hydrogen, or represents straight-chain or branched alkyl with 1 to 12 carbon atoms, or represents in each case straight-chain or branched alkenyl or alkinyl with in each case 3 to 8 carbon atoms, or represents cycloalkyl which has 3 to 8 carbon atoms and is optionally substituted by alkyl with 1 to 4 carbon atoms;
Ar represents phenyl, 2-pyridyl, 3-pyridyl or 4-pyridyl, in each case optionally substituted by substituents independently selected from the group consisting of halogen, cyano, nitro, in each case straight-chain or branched alkyl, alkoxy and alkoxycarbonyl with in each case 1 to 4 carbon atoms in the alkyl parts, in each case straight-chain or branched halogenoalkyl and halogenoalkoxy with in each case 1 to 4 carbon atoms and 1 to 9 identical or different halogen atoms and an —S(O)$_m$—R$^4$ radical,
wherein
R$^4$ represents amino, or represents in each case straight-chain or branched alkyl, alkylamino, dialkylamino or halogenoalkyl with in each case 1 to 4 carbon atoms in the individual alkyl parts and in the case of the halogenoalkyl with 1 to 9 identical or different halogen atoms and
m represents the number 0, 1 or 2; and
X represents oxygen or sulphur;
A represents a straight-chain or branched alkylene bridge which has 1 to 6 carbon atoms and is optionally monosubstituted or polysubstituted by identical or different substituents from the group comprising halogen and phenyl, which is optionally substituted by halogen or alkyl with 1 to 4 carbon atoms;
n represents the number 0 or 1 and
Y represents cyano or the grouping

wherein
X$^1$ represents oxygen or sulphur and
R$^3$ represents hydroxyl, in each case straight-chain or branched alkoxy or alkylthio with in each case 1 to 6 carbon atoms, in each case straight-chain or branched alkenyloxy or alkinyloxy with in each case 3 to 8 carbon atoms, amino, in each case straight-chain or branched alkylamino or dialkylamino with in each case 1 to 6 carbon atoms in the alkyl parts, in each case straight-chain or branched alkenylamino or dialkenylamino with in each case 3 to 8 carbon atoms in the alkenyl parts or straight-chain or branched alkyl-alkenylamino with 1 to 6 carbon atoms in the alkyl part and 3 to 8 carbon atoms in the alkenyl part, or represents an —OM radical,
wherein
M represents one equivalent of an alkaline earth metal cation or alkali metal cation, or represents ammonium which is optionally mono-, di-, tri- or tetrasubstituted by identical or different substituents from the group comprising straight-chain or branched alkyl with 1 to 12 carbon atoms and benzyl.

2. A 5-acylamino-pyrazole derivative according to claim 1, in which
R$^1$ represents hydrogen, nitro, chlorine or bromine,
R$^2$ represents hydrogen, or represents straight-chain or branched alkyl with 1 to 8 carbon atoms, or represents in each case straight-chain or branched alkenyl or alkinyl with in each case 3 to 6 carbon atoms, or represents cycloalkyl which has 3 to 6 carbon atoms and is optionally substituted by methyl, ethyl or isopropyl;
Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, the substituents in each case being cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy) difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R$^4$ radical,
wherein
R$^4$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and
m represents the number 0, 1 or 2, and
X represents oxygen or sulphur;
A represents a bridge member of the formula

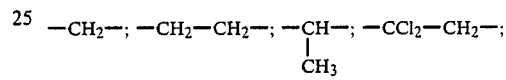

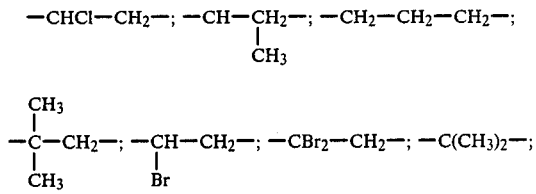

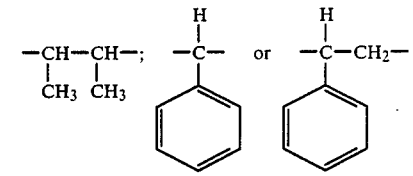

n represents the number 0 or 1 and
Y represents cyano or the grouping

wherein
X$^1$ represents oxygen and
R$^3$ represents hydroxyl, alkoxy with 1 to 3 carbon atoms, alkenyloxy or alkinyloxy with in each case 3 to 6 carbon atoms, amino, alkylamino or dialkylamino with in each case 1 to 3 carbon atoms in each alkyl part, alkenylamino or dialkenylamino with in each case 3 to 6 carbon atoms in each alkenyl part or alkyl-alkenylamino with 1 to 3 carbon atoms in the alkyl part and 3 to 6 carbon atoms in the alkenyl part, or represents an —OM radical,
wherein
M represents one equivalent of a sodium, potassium, calcium, magnesium or barium cation, or represents an isopropylammonium, dimethylbenzylammonium, triethylammonium or tributylammonium ion.

3. A compound according to claim 1, wherein such compound is 5-cyanoacetylamino-1-(2,6-dichloro-4-trifluoromethyl-phenyl)-4-nitro-pyrazole of the formula

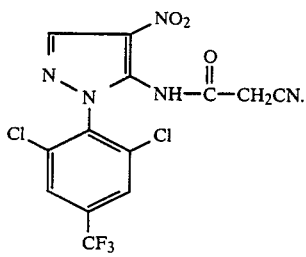

4. A compound according to claim 1, wherein such compound is 1-(2,6-dichloro-4-trifluoromethyl-phenyl)-5-(ethoxycarbonyl-acetamido)-4nitro-pyrazole of the formula

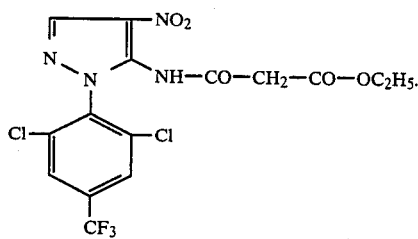

5. A compound according to claim 1, wherein such compound is 1-(2,6-dichloro-4-trifluoromethyl-phenyl)-5-(1-ethoxycarbonyl-propionylamido)-4-nitro-pyrazole of the formula

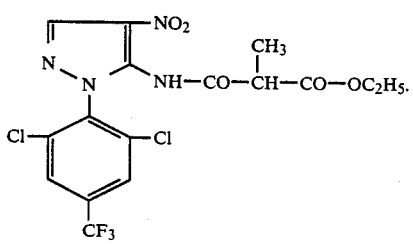

6. A compound according to claim 1, wherein such compound is 1-(2,6-dichloro-4-trifluoromethyl-phenyl)-5-(ethoxalylamido)-4-nitro-pyrazole of the formula

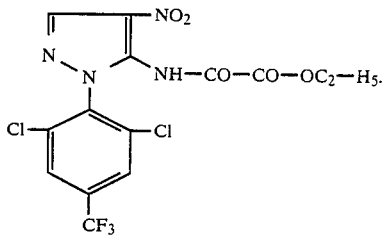

7. A compound according to claim 1, wherein such compound is 1-(2,6-dichloro-4-trifluoromethyl-phenyl)-5-(sodiooxalylamido)-4-nitro-pyrazole of the formula

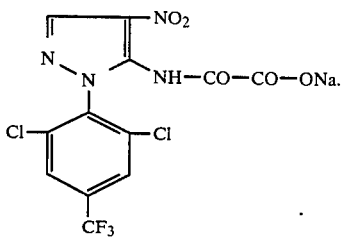

8. A herbicidal composition comprising a herbicidally effective amount of a compound according to claim 1 and a diluent.

9. A method of killing unwanted vegetation which comprises applying to such vegetation or to a locus from which it is desired to exclude such vegetation a herbicidally effective amount of a compound according to claim 1.

10. The method according to claim 9, wherein such compound is
5-cyanoacetylamino-1-(2,6-dichloro-4-trifluoromethyl-phenyl)-4-nitro-pyrazole,
1-(2,6-dichloro-4-trifluoromethyl-phenyl)-5-(ethoxycarbonyl-acetamido)-4-nitro-pyrazole,
1-(2,6-dichloro-4-trifluoromethyl-phenyl)-5-(1-ethoxycarbonyl-propionylamido)-4-nitro-pyrazole,
1-(2,6-dichloro-4-trifluoromethyl-phenyl)-5-(ethoxalylamido)-4-nitro-pyrazole, or
1-(2,6-dichloro-4-trifluoromethyl-phenyl)-5-(sodiooxalylamido)-4-nitro-pyrazole.

11. A plant growth-regulating compositon comprising a plant-growth-regulating effective amount of a compound according to claim 1 and a diluent.

12. A method of regulating the growth of plants which comprises applying to such plants or to a locus in which such plants are growing or are to be grown a plant growth-regulating effective amount of a compound according to claim 1.

13. The method according to claim 12, wherein such compound is
5-cyanoacetylamino-1-(2,6-dichloro-4-trifluoromethyl-phenyl)-4-nitro-pyrazole,
1-(2,6-dichloro-4-trifluoromethyl-phenyl)-5-(ethoxycarbonyl-acetamido)-4-nitro-pyrazole,
1-(2,6-dichloro-4-trifluoromethyl-phenyl)-5-(1-ethoxycarbonyl-propionylamido)-4-nitro-pyrazole,
1-(2,6-dichloro-4-trifluoromethyl-phenyl)-5-(ethoxalylamido)-4-nitro-pyrazole, or
1-(2,6-dichloro-4-trifluoromethyl-phenyl)-5-(sodiooxalylamido)-4-nitro-pyrazole.

* * * * *

UNITED STATES PATENT AND TRADEMARK OFFICE
CERTIFICATE OF CORRECTION

PATENT NO. : 4,772,310

DATED : September 20, 1988

INVENTOR(S) : Jörg Stetter, et al

It is certified that error appears in the above-identified patent and that said Letters Patent is hereby corrected as shown below:

| | |
|---|---|
| Title Page, Title, line 4, and Col. 1, line 5 | After "GROWTH" insert --REGULATORS-- |
| Col. 3, line 54 and Col. 34, line 52 | Delete "arylpyrazoles" and substitute --aryl-pyrazoles-- |
| Col. 4, line 64 | Delete "r$^1$" and substitute --R$^1$-- |
| Col. 8, line 50 | Delete "chloroethyl" and substitute --chloromethyl-- |
| Col. 23, Table 1, line 3 under "Y" | Delete "COCH$_3$" and substitute --COOCH$_3$-- |
| Col. 44, line 31 | Correct spelling of --hydrolysis-- |
| Col. 44, lines 38 and 39 | Correct spelling of --phospholipids-- |
| Col. 45, line 15 | Delete "acic" and substitute --acid-- |
| Col. 48, line 46 | Correct spelling of --pyrazole-- |
| Col. 55, Example 27, first formula under "Ar" | 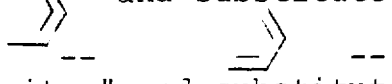 |
| Col. 65, line 25 | Delete "4nitro" and substitute --4-nitro-- |

Signed and Sealed this

Sixteenth Day of May, 1989

Attest:

DONALD J. QUIGG

Attesting Officer

Commissioner of Patents and Trademarks